US00RE49516E

(19) United States
(12) Reissued Patent
Caclin

(10) Patent Number: US RE49,516 E
(45) Date of Reissued Patent: May 2, 2023

(54) SYRINGE AND METHOD FOR ASSEMBLING IT

(71) Applicant: GUERBET, Villepinte (FR)

(72) Inventor: Jérôme Caclin, Venissieux (FR)

(73) Assignee: GUERBET, Villepinte (FR)

(21) Appl. No.: 17/313,682

(22) Filed: May 6, 2021

Related U.S. Patent Documents

Reissue of:
(64) Patent No.: 10,744,266
Issued: Aug. 18, 2020
Appl. No.: 15/742,430
PCT Filed: Jul. 8, 2016
PCT No.: PCT/EP2016/066319
§ 371 (c)(1),
(2) Date: Jan. 5, 2018
PCT Pub. No.: WO2017/005914
PCT Pub. Date: Jan. 12, 2017

(30) Foreign Application Priority Data

Jul. 8, 2015 (FR) ..... 1556463

(51) Int. Cl.
*A61M 5/315* (2006.01)

(52) U.S. Cl.
CPC ..... *A61M 5/31505* (2013.01); *A61M 5/31501* (2013.01); *A61M 2005/31506* (2013.01); *A61M 2005/31508* (2013.01)

(58) Field of Classification Search
CPC ..... A61M 5/31505; A61M 5/31501; A61M 5/3151; A61M 2005/31506; A61M 2005/31508
See application file for complete search history.

(56) References Cited

U.S. PATENT DOCUMENTS 4,153,056 A * 5/1979 Silver ..... A61M 5/31551 604/211
5,803,918 A 9/1998 Vetter et al.
9,089,671 B2 7/2015 Stout et al.
(Continued)

FOREIGN PATENT DOCUMENTS

CN 103998090 A 8/2014
DE 102007014418 A1 9/2008
(Continued)

OTHER PUBLICATIONS

Notice of Reasons for Rejection for Patent Application No. 2018-500544 dated Feb. 16, 2021, English Translation, 7 pages.
(Continued)

*Primary Examiner* — Beverly M Flanagan
(74) *Attorney, Agent, or Firm* — Thompson Coburn LLP

(57) ABSTRACT

A syringe comprising: a body delimiting a chamber; a piston able to slide in the chamber of the body along a longitudinal axis of the syringe, wherein the piston comprises a rod, a head, and a finger rest, which are all in one piece; and a deformable retention device designed to prevent the piston from leaving the body entirely, wherein the retention device is force-fitted in the chamber, extends around the piston over an angular sector strictly greater than 180° when it is in the assembled position, and has protruding external ribs which extend parallel to the longitudinal axis and are plastically deformable when the retention device is assembled in the chamber.

28 Claims, 7 Drawing Sheets

(56) References Cited

U.S. PATENT DOCUMENTS

| | | | | |
|---|---|---|---|---|
| 2006/0264837 | A1* | 11/2006 | Bloom | A61M 5/31501 604/208 |
| 2008/0281266 | A1* | 11/2008 | Walton | A61M 5/5013 604/110 |
| 2010/0089185 | A1 | 4/2010 | Schliemann | |
| 2013/0090608 | A1* | 4/2013 | Stout | A61M 39/00 29/525.08 |
| 2014/0276592 | A1* | 9/2014 | Mottola | A61M 5/31505 604/506 |
| 2014/0336591 | A1 | 11/2014 | Skaper et al. | |

FOREIGN PATENT DOCUMENTS

| | | | |
|---|---|---|---|
| EP | 2801382 | A1 | 11/2014 |
| FR | 2788985 | A1 | 8/2000 |
| JP | 54-010177 | A | 6/1799 |
| JP | 51-112396 | U | 9/1976 |
| JP | 2004-357923 | A | 12/2004 |
| WO | 2006121513 | A2 | 11/2006 |
| WO | 2009019673 | A2 | 2/2009 |
| WO | 2014082412 | A1 | 6/2014 |
| WO | 2014121307 | A1 | 8/2014 |

OTHER PUBLICATIONS

International Search Report and Written Opinion for PCT/EP2016/066319 dated Sep. 7, 2016.
English Translation of Chinese Office action issued in related Chinese Application 2016800451253 dated Dec. 12, 2019, 7 pages.
Russian Office action issued in related Russian Application 2018104728/14(007076) dated Nov. 28, 2019, 4 pages.

* cited by examiner

SYRINGE AND METHOD FOR ASSEMBLING IT

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is *a reissue application of U.S. application Ser. No. 15/742,430, filed Jan. 5, 2018, now U.S. Pat. No. 10,744,266, issued Aug. 18, 2020, which is* a U.S. National Phase application of PCT/EP2016/066319, filed on Jul. 8, 2016, claiming the benefit of French Application No. 1556463, filed on Jul. 8, 2015, each of which is incorporated herein by reference in its entirety.

The present invention concerns a syringe and a method for assembling a syringe of this kind.

The invention concerns in particular rigid-material syringes for medical use that are filled by pressure.

In the conventional manner a syringe comprises a cylindrical body delimiting a chamber in which a piston is received.

A syringe can be filled by suction, i.e. the user pulls on the piston of this syringe to aspirate a liquid manually. The user can regulate their force and stop pulling on the piston when it arrives at its end of travel in order to prevent the piston leaving the body of the syringe entirely.

A syringe can also be filled by pressure, i.e. it is connected to a container which feeds the liquid into the syringe when pressure is exerted on it. It is very often difficult to define accurately the pressure to be exerted on the container to fill the syringe as required and there is therefore a high risk of excess pressure exerted on the container causing the piston to leave the body of the syringe entirely.

In the case of c-TACE (conventional Trans Arterial Chemo Embolization) procedures, for example, the syringe is used in combination with a medical valve and is filled by pressure, i.e. the syringe is connected to a second syringe that feeds the liquid into the first syringe. The user does not manipulate the first syringe and so does not realize the effect on the first syringe of their force when pushing on the piston of the second syringe. There is therefore a risk of the piston of the first syringe being ejected. The procedure must then be started again from scratch since the conditions of sterility thereof are no longer assured. Moreover, this exposes the practitioner to potentially hazardous products, for example cytotoxic products in the case of c-TACE.

U.S. Pat. No. 5,803,918 discloses a syringe the body of which is equipped with an external retaining ring including a finger curved into the chamber of the body of the syringe. The finger immobilizes the piston, preventing it from being separated from the body of the syringe. The contact surface between the piston and the retaining ring is formed by the end of the finger, which is of small size. The efficacy of the immobilization of the piston is therefore limited, since this system gives only tactile feedback that indicates to the practitioner when to stop pulling on the piston in the case of filling by suction but does not provide a sufficient warning in the case of filling by pressure. This system therefore does not prevent the piston from being inadvertently caused to leave the body of the syringe.

There is therefore a need for syringes enabling their piston to be prevented from leaving their body entirely. This issue moreover runs up against the fact that there exist on the market syringes with bodies made of deformable plastic material and syringes with bodies made of rigid and therefore non-deformable plastic material.

When the aim is to retain the piston of a syringe having a body made of rigid plastic material when the piston is pushed toward the exit from the body of the syringe, the efficacy of retention is either limited by reason of insufficient contact interference between the piston and a device fastened to the syringe body or achieved by costly and complex arrangements based on a piston comprising a plurality of separate parts and/or a complicated initial assembly of the piston and the syringe body.

EP 2 801 382 discloses a syringe with a body made of plastic material that is deformable because the head of the piston inserted in this syringe does not include a seal. A non-deformable device termed a "closing body" is inserted in this syringe and is made up of two parts connected together by a thin hinge and by a locking system attaching the two parts together once arranged around the piston. This locking system prevents the device from unfolding, i.e. prevents the two parts moving away from each other, when this device is inserted in the body of the syringe. The retention of the piston by this device is exclusively the result of the transverse engagement in lateral openings of the syringe body of two projecting clips carried respectively by the two parts of the device: an arrangement of this kind has poor mechanical performance and does not make it possible to prevent ejection of the piston out of the syringe body in the case of filling by pressure with an uncontrolled force.

One object of the invention is therefore to propose a new syringe enabling simple and effective retention of the piston in the syringe body in use.

To this end the subject of the invention is a syringe as defined in claim 1.

Thanks to the invention the piston is efficaciously immobilized in the body of the syringe by the retention device, which is easily assembled by virtue of being force-fitted in the body of the syringe and has a large area of contact with the piston to retain it.

Advantageous but non-obligatory aspects of the invention are specified in the dependent claims.

Another aspect of the invention concerns a method as defined in claim 14 of assembling a syringe. An optional advantageous arrangement is defined in claim 15.

The invention will be better understood and other aspects thereof will become more clearly apparent in the light of the following description of a syringe and its method of assembly, both according to the invention, given by way of example only and with reference to the drawings, in which.

Figure 1:
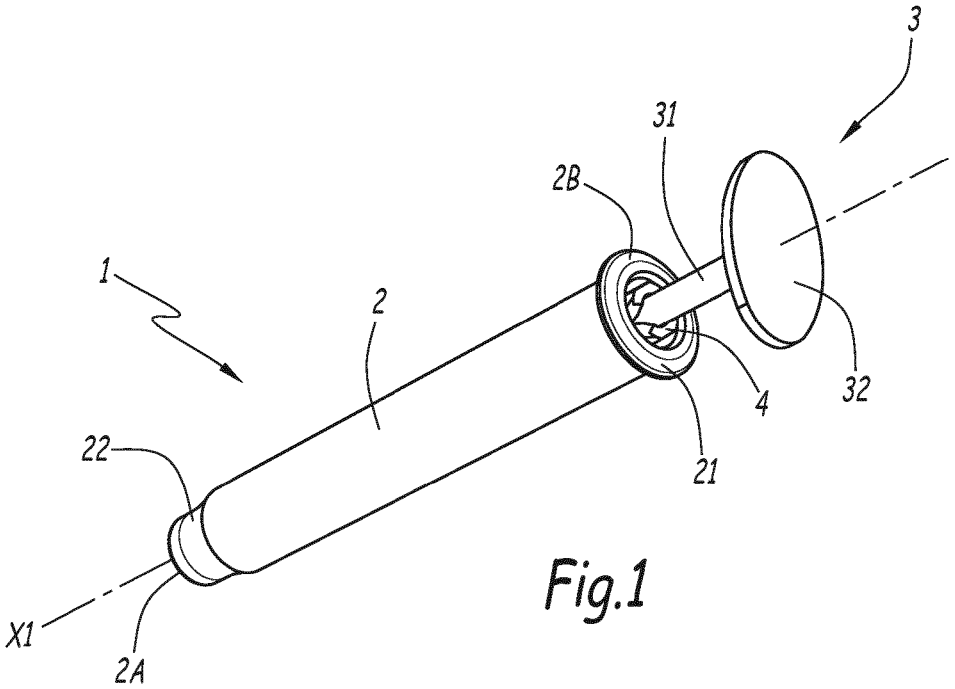
FIG. 1 is a perspective view of a syringe conforming to the invention.
Figure 2:
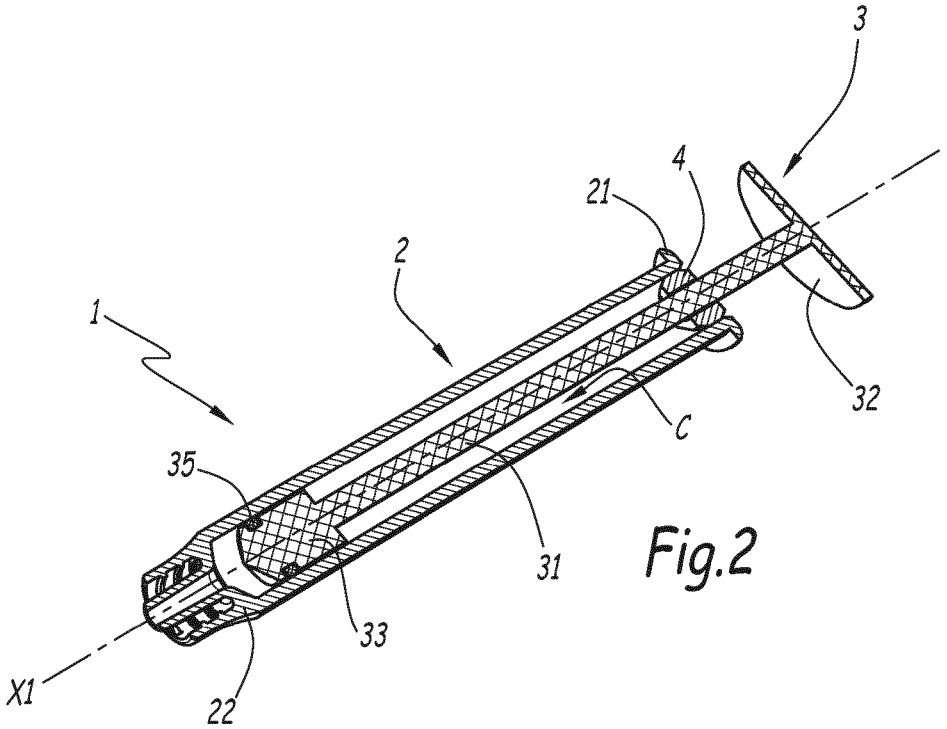
FIG. 2 is a perspective view in longitudinal section of the syringe from FIG. 1.
Figure 3:
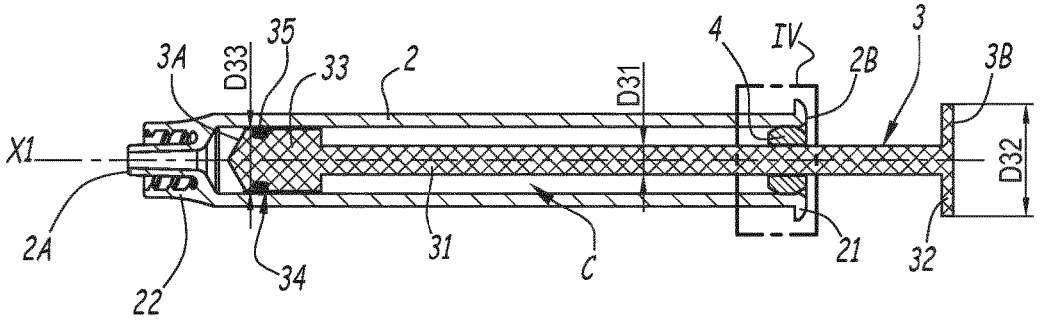
FIG. 3 is a longitudinal section of the syringe from FIG. 1.
Figure 4:
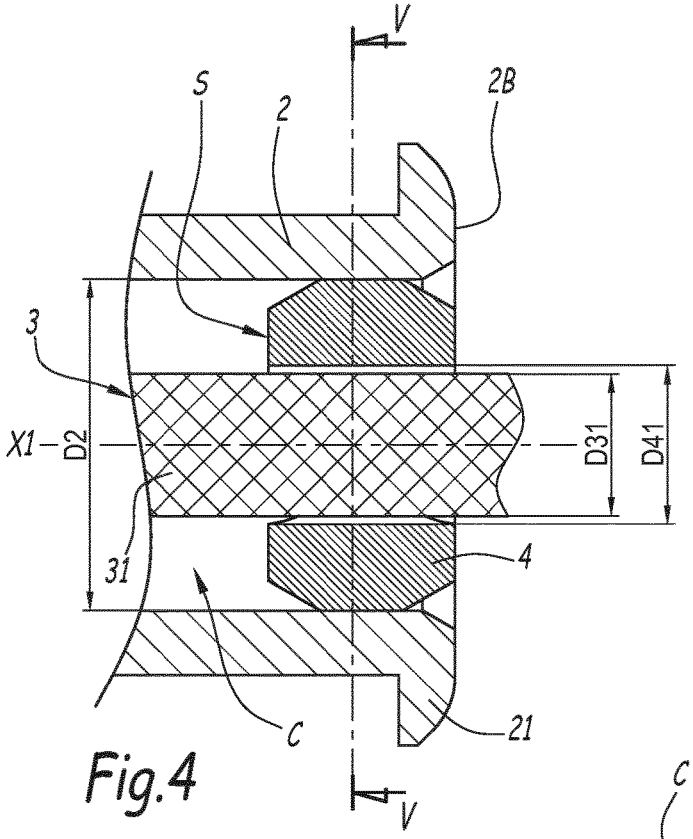
FIG. 4 is a view to a larger scale of the detail IV from FIG. 3.
Figure 5:
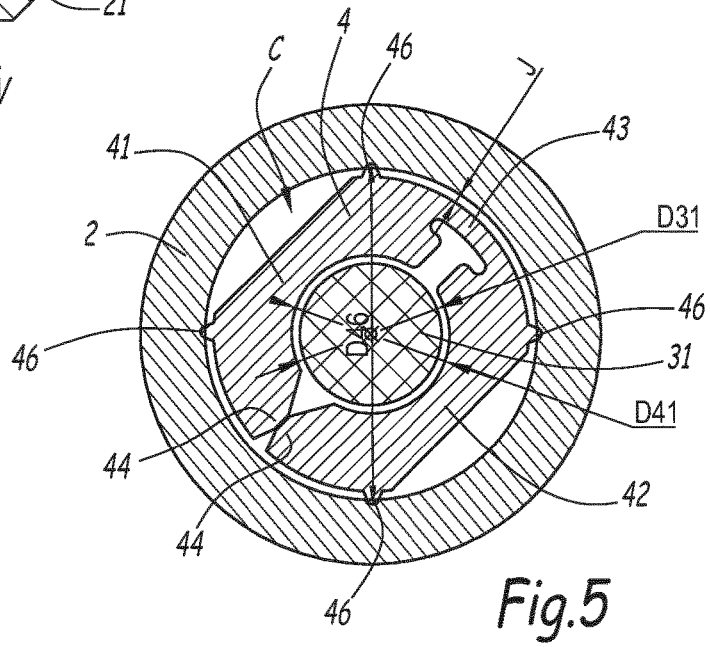
FIG. 5 is a section taken along the line V-V in FIG. 4.

The syringe 1 shown in FIGS. 1 to 5 comprises a preferably cylindrical body 2, a piston 3 and a retention device 4. The syringe 1 extends lengthwise along a longitudinal axis X1 which is an axis of revolution for the piston 3 and the body 2.

The body 2 is of tubular shape and delimits a chamber C in which the piston 3 is mounted to slide along the axis X1. D2 denotes an inside diameter of the body 2 equal to the diameter of the chamber C. The piston 3 is preferably mounted with a sliding pivot connection, i.e. as well as being able to slide it is able to pivot in the body 2 of the syringe 1. A first head 22 of the body 2 forms a first end 2A of the body 2. The head 22 is equipped with an end cone also termed a "Luer cone" designed to enable the connection of the syringe with another device, the latter device notably conforming to one of the usual Luer standards, such as ISO 594 and ISO 80369, without the indication of those standards being limiting. Opposite the head 22, along the axis X1, the body 2 includes an annular external flange 21 that forms a second end 2B of the body 2. The annular external flange 21 is preferably not intended to be used for holding the syringe. The annular external flange 21 preferably projects radially outward less than 5 mm, preferably less than or up to 2 mm or even more preferably strictly less than 2 mm.

The piston 3 includes a rod 31 of diameter D31 extending along the axis X1. A first longitudinal end 3A of the piston 3 is formed by a second head 33 of diameter D33 strictly greater than the diameter D31 of the rod 31. The head 33 preferably includes a peripheral annular groove 34 in which a sealing element is disposed. The sealing element 35 is preferably chosen from at least one O-ring seal and one lip seal. The lip seal is chosen from a double-lip seal and a triple-lip seal. The sealing element 35 is even more preferably an O-ring seal. The sealing element 35 can consist of a plurality of O-ring seals, for example two O-ring seals.

As an alternative, the sealing element 35 forms an integral part of the head 33 of the piston 3 and is for example produced by injection molding at the same time as the piston 3 or by overmolding. In this embodiment the sealing element therefore takes the form of one or more annular protuberances on the surface of the head 33 of the piston 33.

A finger rest 32 forms a second longitudinal end 3B of the piston 3 opposite the head 33.

Overall, the finger rest 32 extends across the axis X1. Projected onto a geometrical plane perpendicular to the axis X1 the finger rest 32 can have any peripheral contour, for example of round, elliptical, circular, rectangular or square shape. The aforementioned peripheral contour of the finger rest is preferably of elliptical shape. D32 denotes the smallest transverse dimension of the finger rest 32, i.e. its minimum dimension in a geometrical plane perpendicular to the axis X1.

Generally speaking, on its face axially opposite the rod 31 the finger rest 32 is flat, convex or concave. The finger rest 32 is preferably convex or concave. In one particular embodiment when the syringe 1 has a chamber C of volume less than or equal to 3 mL the finger rest 32 is convex. In another particular embodiment when the syringe 1 has a chamber C of volume strictly greater than 3 mL and less than or equal to 15 mL the finger rest 32 is convex. In another particular embodiment when the syringe 1 has a chamber C of volume strictly greater than 15 mL the finger rest is concave. In another embodiment of the invention when the syringe 1 has a chamber C of volume greater than or equal to 20 mL the finger rest 32 is concave. By a convex finger rest is preferably meant in the context of the present invention that the finger rest follows the shape of the fingers that will be placed on it. By a concave finger rest is preferably meant in the context of the present invention that the finger rest follows the shape of the palm of the hand that will be placed on it.

The piston 3 is of unitary construction, in other words the rod 31, the head 33 and the finger rest 32 are in one piece. Apart from the sealing element or elements 35, the piston 3 is not the result of assembling a plurality of elements.

The retention device 4 takes the form of an open ring and is deformable so that it can be mounted around the rod 31 of the piston 3. The retention device 4 is preferably deformable only when mounting it on the rod 31 of the piston 3. The retention device 4 preferably has no arrangement locking it in the fixed form of a ring closed on itself, which enables the retention device 4 to exert, notably through structural resilience, a radial force toward the outside of the body 2 of the syringe 1 once it is inserted in said body.

The retention device 4 is mounted around the piston 3 which is then inserted into the chamber C. The retention device 4 surrounding the piston 3 is then force-fitted into the body 2, inside the chamber C, from the end 2B of the body 2.

The retention device 4 is made of plastic material, for example, and can be manufactured by any technique known to the person skilled in the art and notably by injection molding or extrusion.

Figure 6:
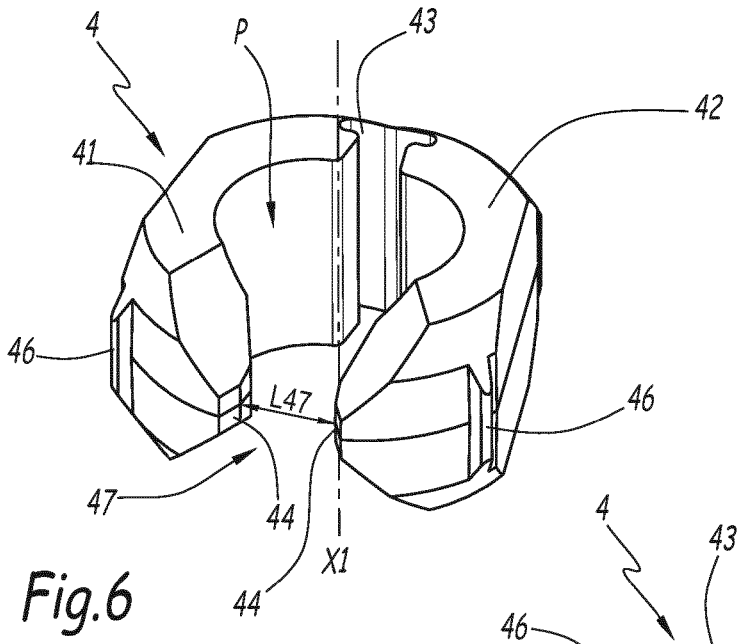
FIG. 6 is a perspective view of a retention device forming part of the syringe from FIG. 1 in a free position.

FIG. 6 shows the retention device 4 in a free position, i.e. when no external mechanical load is applied to it. The free position is that obtained at the time of injection molding the plastic.

Figure 8:
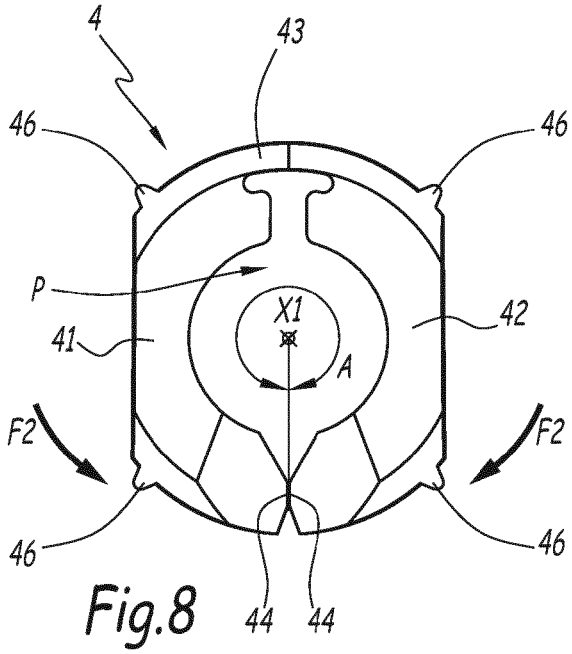
FIG. 8 is a front view of the retention device from FIG. 6 in an assembled position.

The retention device 4 includes two C-shaped or part-ring-shaped parts 41 and 42 that delimit between them a passage P intended to receive the rod 31 of the piston 3. Each part 41 and 42 includes an interior surface of part-cylindrical shape centered on the axis X1 with a functional clearance so as to define a globally cylindrical shape for the passage P when the retention device 4 is in an assembled position shown in FIG. 8.

In the free position the ends 44 of each part 41 and 42 are spaced from each other by a non-zero distance so that the retention device 4 forms an open ring. An entry opening 47 into the passage P is delimited between the ends 44 of the parts 41 and 42. The parts 41 and 42 are connected to each other by a deformable thinned area 43 thin enough to enable a user to move the parts 41 and 42 away from or toward each other.

The thinned area 43 preferably has a thickness strictly greater than 0.6 mm or even between 0.7 and 3 mm inclusive or even between 0.7 and 2.5 mm inclusive or between 0.7 and 1 mm inclusive or else between 2 and 2.5 mm inclusive. In one particular embodiment when the syringe 1 has a volume of the chamber C less than or equal to 3 mL the deformable thinned area 43 has a thickness between 0.7 and 1 mm, preferably of 0.7 mm. In one particular embodiment when the syringe 1 has a volume of the chamber C greater than or equal to 20 mL the deformable thinned area 43 has a thickness between 2 and 2.5 mm, preferably of 2.2 mm.

This thickness of the thinned area 43 induces a spring effect between the parts 41 and 42. This spring effect is more preferably produced in a durable manner, i.e. throughout the use of the syringe 1, after the force-fitting of the retention device 4. The deformable thinned area 43 therefore remains "responsive" once mounted in the body 2 of the syringe. Once it has been stressed after force-fitting the retention device 4 in the body 2 of the syringe, this thinned area 43 is not subjected to any plastic deformation that is irreversible, i.e. that would result from exceeding the elastic limit of this thinned area 43. The spring effect induces a specific radial force enabling better retention of the retention device inside the body of the syringe.

A denotes an angular sector centered on the axis X1, i.e. on the geometrical center of the passage P, and delimited by the ends 44 of the retention device 4. The angular sector A extends to either side of the opening 47.

Figure 9:
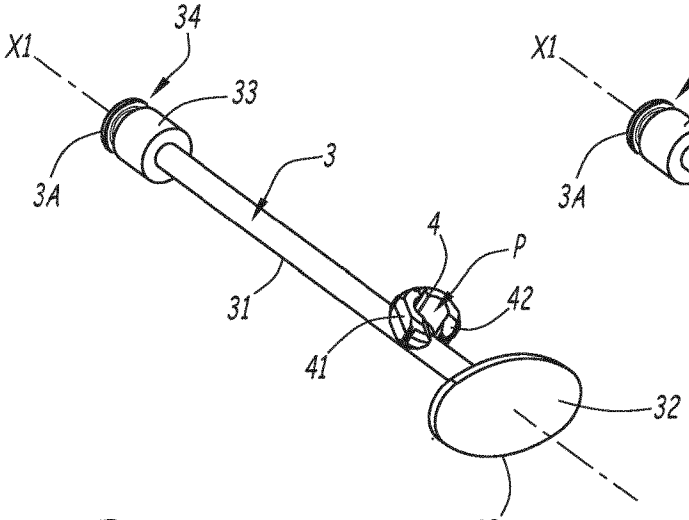
Figure 12:
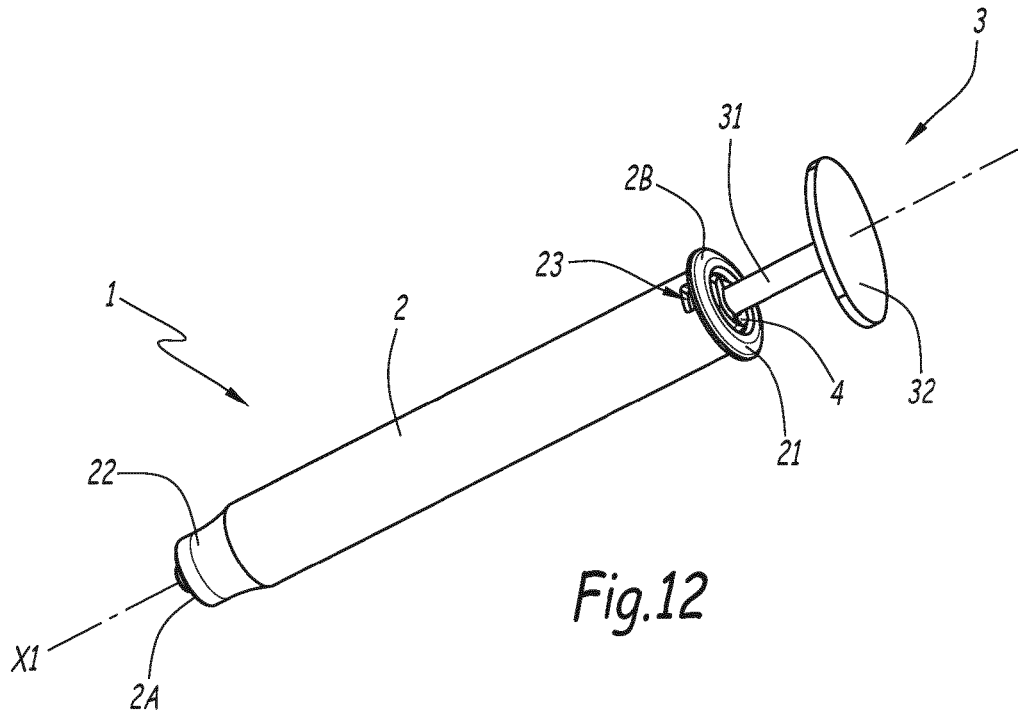
FIGS. 12 to 17 are views respectively similar to FIGS. 1, 3, 4, 6, 7 and 8 showing a variant of the syringe conforming to the invention.
Figure 13:
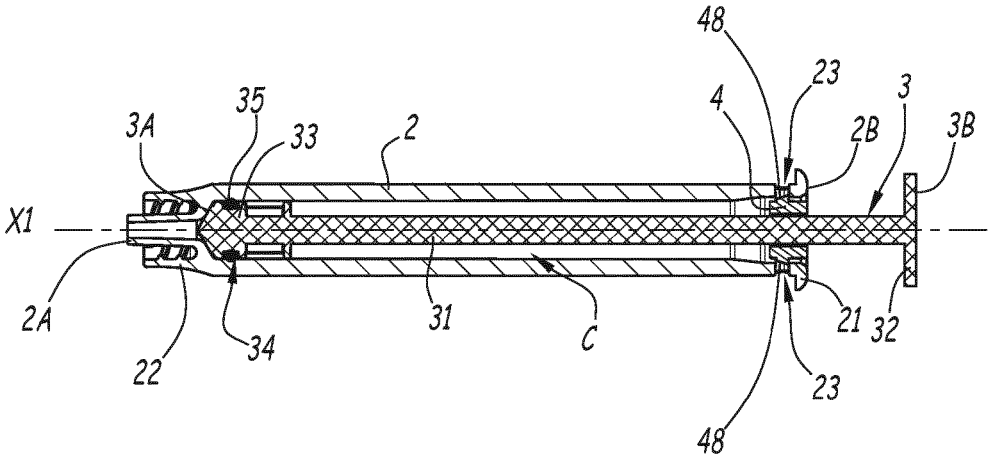
Figure 14:
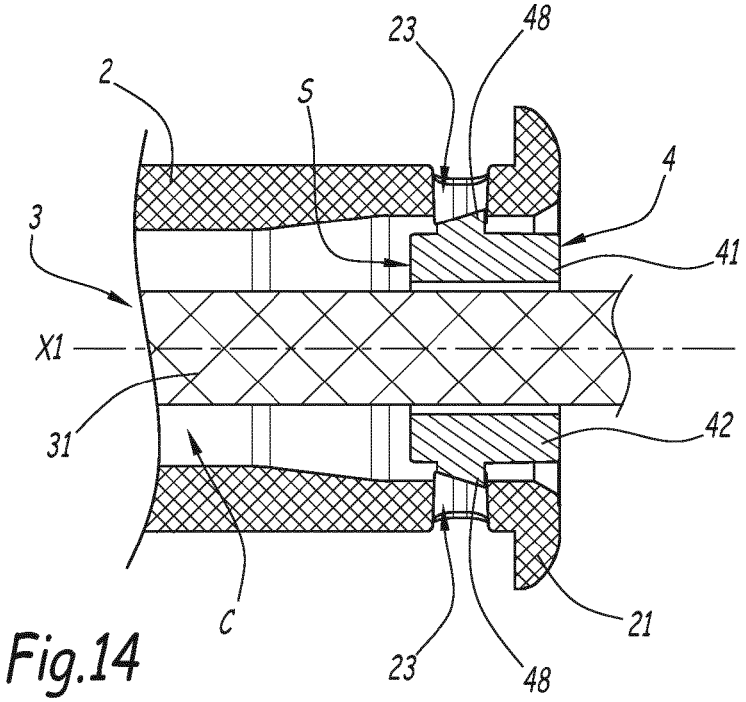
Figure 15:
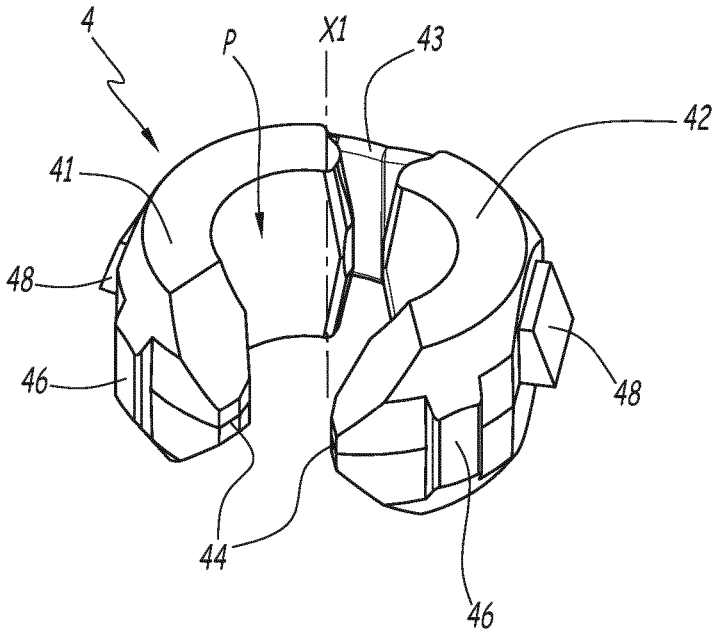

FIG. 9 shows the retention device 4 in a first mounting position in which it is brought up against the rod 31 of the piston 3. The opening 47 of the passage P of the retention device 4 is positioned against the rod 31. The width L47 of the opening 47 as measured between the ends 44 of the parts 41 and 42 is less than the diameter D31 of the rod 31 of the piston 3.

Figure 7:
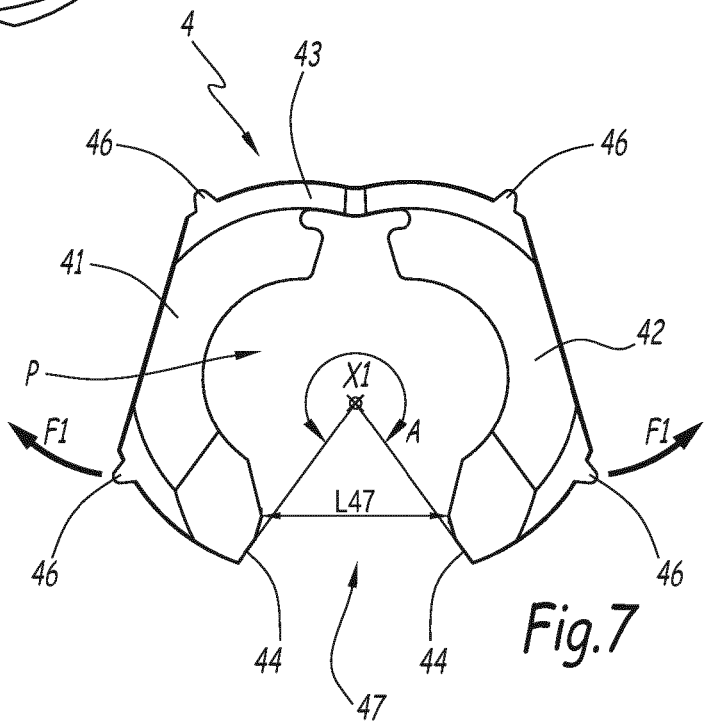
FIG. 7 is a front view of the retention device from FIG. 6 in a mounting position.
Figure 10:
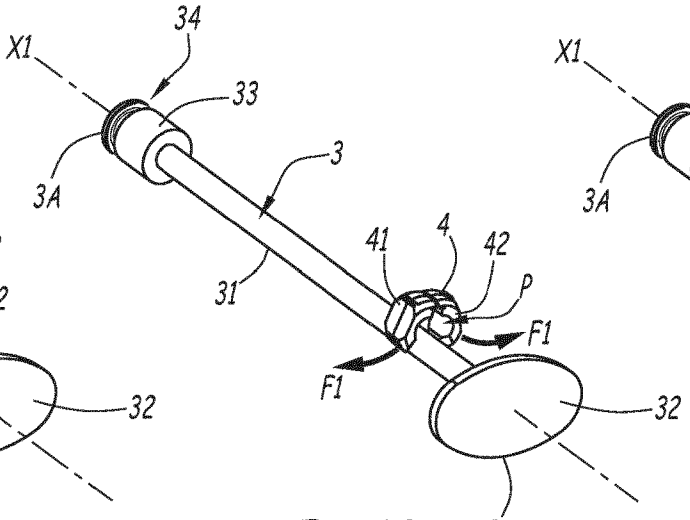

As can be seen in FIG. 10, to allow the insertion of the rod 31 in the passage P of the retention device 4 the parts 41 and 42 of the retention device 4 are moved away from each other as shown by the arrows F1 so as to enlarge the opening 47 of the passage P. It is then possible to position the rod 31 in the passage P. In this position of the retention device 4 shown in FIG. 7 the width L47 of the opening 47 is greater than or equal to the diameter D31 of the rod 31.

Figure 11:
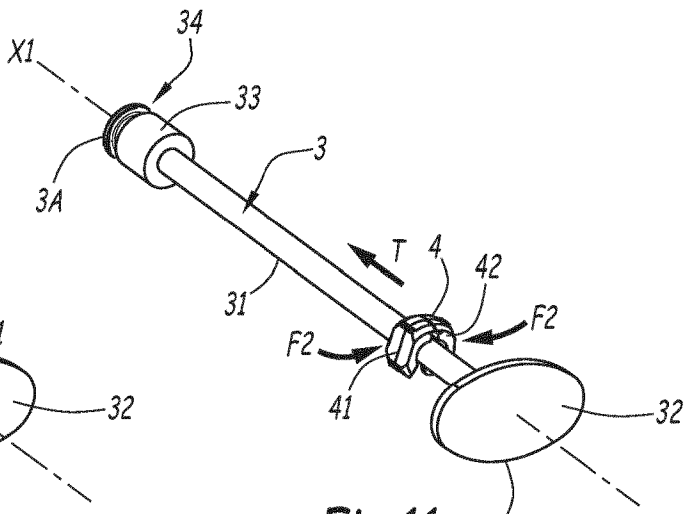
FIGS. 9 to 11 are perspective views of a piston of the syringe from FIG. 1 and the retention device in three successive assembly configurations.

The parts 41 and 42 are then moved toward each other as shown by the arrows F2 in FIG. 11, which causes the width L47 to be less than the diameter D31 of the rod 31 again. The movement toward each other of the parts 41 and 42 is continued until the retention device 4 in the assembled position is passed. In this assembled position of the retention device shown in FIG. 5 the ends 44 are in contact with each other, closing the opening 47 of the passage P, which is then of substantially cylindrical shape, as mentioned above and as can be seen in FIG. 8. The retention device 4 then surrounds the rod 31 of the piston over 360°.

In the context of the invention, in the assembled position, the angular sector A is strictly greater than 180°, preferably greater than 270°, more preferably greater than 300°, even more preferably equal to 360°.

The assembly formed by the piston 3 and the retention device 4 is then force-fitted in the body 2 of the syringe 1 by a movement T of axial translation, i.e. coaxially with the axis X1.

The retention device 4 includes protruding ribs 46 which extend parallel to the axis X1. In other words, each rib 46 takes the form of an elongate protrusion the longitudinal direction of which is parallel to the axis X1. Each rib thus extends lengthwise between the opposite axial ends of the retention device 4, in particular in the main region of the latter connecting its two axial ends.

In the example shown the first part 41 carries from two to four first ribs 46 and the second part 42 carries from two to four other ribs 46. The retention device 4 therefore includes four to eight ribs. When the syringe 1 has a volume of the chamber C less than or equal to 3 mL the retention device 4 preferably includes two ribs on each part 41 and 42, i.e. four ribs in total. When the syringe 1 has a volume of the chamber C greater than or equal to 20 mL the retention device 4 preferably includes more than two ribs, more preferably four ribs on each part 41 and 42. In this embodiment the retention device 4 therefore includes more than four ribs, preferably eight ribs in total. More generally, the ribs 46 are preferably disposed on the retention device 4 so as to be at a distance from each other around the axis X1.

At the level of each rib a maximum outside transverse dimension D46 of the retention device 4 is strictly greater than the diameter D2 of the chamber C of the body 2. The difference between the dimension D46 and the diameter D2 is preferably chosen in order to obtain a sufficient force-fitting force to retain the piston 3 when filling the syringe 1 by pressure. The dimension D46 is radial with respect to the axis X1.

Outside the ribs 46 the maximum transverse outside dimension of the retention device 4 is strictly less than the diameter D2 of the chamber C of the body 2, providing a functional clearance J.

The ribs 46 are plastically deformed when force-fitting the retention device 4 in the chamber C. The corresponding crushing of them enables the retention device 4 to be retained firmly in the body 2 of the syringe 1.

According to the variant shown in FIGS. 12 to 17 the retention device 4 further includes at least one clip 48 on one or the other of the parts 41 and 42 of the device. Two clips 28 are preferably provided, one on the part 41 and one on the part 42 of the retention device 4. In the assembled position of the retention device 4 the or each clip 48 is received in a housing provided for this purpose in the body 2 of the syringe 1. The or each housing 23 leads into the chamber C of the body 2 of the syringe 1 and extends over at least part of the radial thickness of the wall of this body 2. As in the example that FIGS. 12 to 15 concern, the or each housing 23 preferably passes completely through the wall of the body 2 of the syringe 1.

When force-fitting the retention device 4 in the chamber C the or each clip 48 is forcibly engaged axially inside the chamber C, being urged radially toward the axis X1 by the wall of the body 2 of the syringe 1, until reaching the housing or one of the housings 23: on release of this stress, the clip 48 then engages in the housing 23 in a manner transverse or even radial to the axis X1. According to a preferred embodiment, used in the example that FIGS. 12 to 15 concern, the or each clip 48 has in section in a plane containing the axis X1 an external profile converging toward the head 22 of the body 2 of the syringe. In all cases the clip or clips 48 reinforces or reinforce the ribs 46 to improve the retention over time of the retention device 4 inside the body 2 of the syringe 1.

Figure 16:
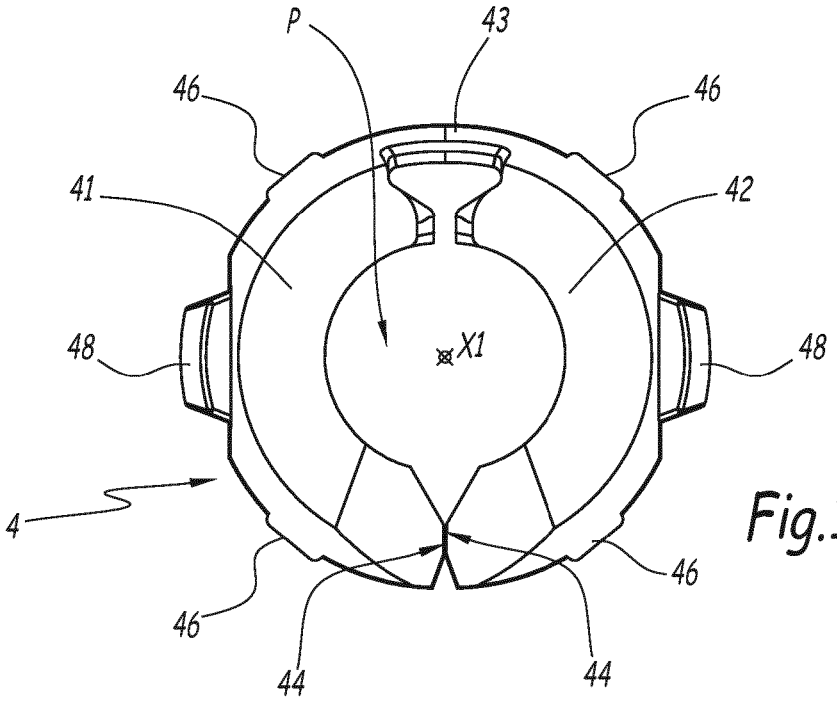
Figure 17:
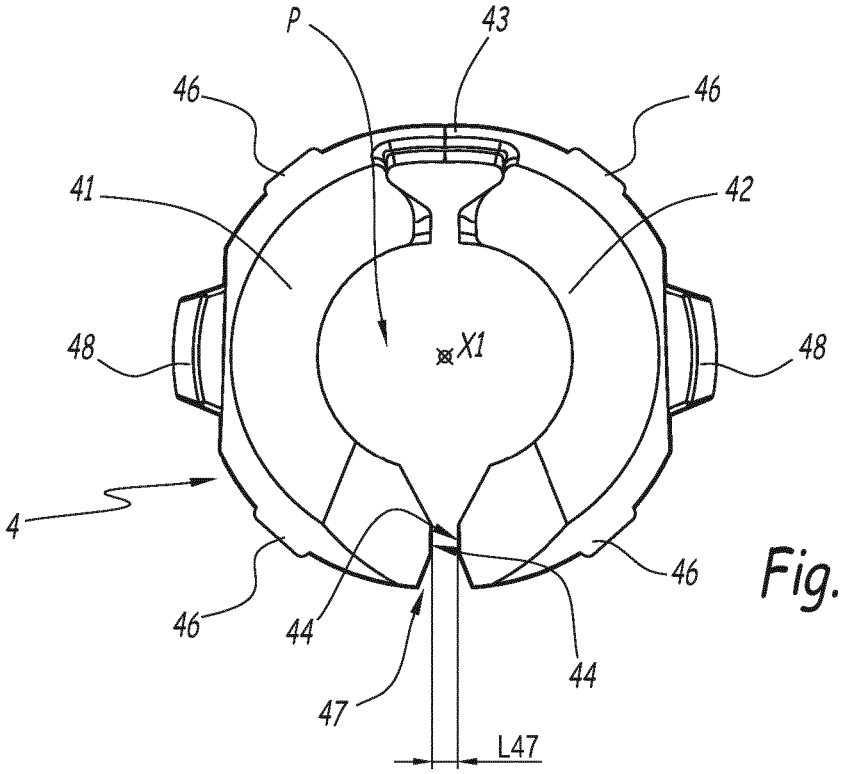

Moreover, and independently of the arrangements relating to the clips 48, the retention device 4 that FIGS. 12 to 17 concern is such that in the assembled position of this retention device the ends 44 of the parts 41 and 42 are not in contact with each other, i.e. are spaced apart from each other by a non-zero distance, for example a distance of a few tenths of a millimeter, as can be seen in FIG. 17. In the assembled position of the retention device the passage P, which is then of substantially cylindrical shape as mentioned above, therefore has its opening 47 almost entirely but totally closed: as indicated in FIG. 17 the width L47 of this opening 47 therefore has a non-zero value which is of course less than the diameter D31 of the rod 31 of the piston 3. Before reaching this assembled position, in other words while force-fitting the retention device 4, the ends of the parts 41 and 42 are moved toward each other until, where applicable, they touch, as shown in FIG. 16, which facilitates placing the retention device 4 inside the chamber C of the body 2 of the syringe 1. The ends 44 spread apart again once the retention device is in the assembled position as a result of the propensity of this device to revert to its free position from FIG. 15 and this enables the device to strengthen its radial retention inside the body of the syringe.

The body 2 of the syringe 1 is made from a plastic material having a Young's modulus (also termed the modulus of elasticity or modulus of mechanical retraction) strictly greater than 1600 MPa, preferably greater than or equal to 1800 MPa, even more preferably equal to 1900 MPa. This plastic material has the property of being rigid and therefore of not being deformable. A plastic material having such a Young's modulus is preferably chosen from methyl methacrylate-acrylonitrile-butadiene styrene (MABS) copolymers, polycarbonates (PC), polymethylmethacrylate (PMMA), polyamides (PA), preferably PA11 and PA12, polysulfone (PSU), cyclo-olefin copolymers (COC) and cyclo-olefin polymers (COP). These plastic materials also have the advantage of being transparent.

The body 2 and the retention device 4 are preferably made of the same material. The body 2 and the retention device 4 are more preferably made of materials enabling the friction between them to be increased. The body 2 and the retention device 4 are even more preferably made from a material and with a surface state increasing the friction between these two parts. An example of a surface state increasing the friction between the body 2 and the retention device 4 is achieved by subjecting the two parts to "mirror finish" polishing.

The retention device 4 includes a surface S perpendicular to the axis X1 and facing toward the chamber C of the body 2, designed to come into contact with the head 33 of the piston 3 when the latter is in its rear position in order to prevent it leaving the body 2 entirely. The surface S has an open ring shape in the free position and a closed ring shape in the assembled position.

The passage P of the retention device 4 in the assembled position has a diameter D41 that is strictly less than the diameter D33 of the head of the piston 3. The greater the difference between the diameters D41 and D33, the larger the surface S. This is favorable to the retention of the piston 3 in the chamber C.

The diameter D33 is preferably at least 10% greater, preferably at least 25% greater, than the diameter D41.

This diameter difference is particularly advantageous for a syringe 1 in which the chamber C has a small volume, of the order of 1 mL. The volume of the chamber C is preferably less than 25 mL, preferably less than or equal to 20 mL, more preferably less than or equal to 3 mL and even more preferably less than or equal to 1 mL.

The invention avoids any relation between the diameter D41 of the passage P of the retention device 4 in the assembled position on the one hand and the diameters D33 of the head 33 of the piston 3 and D32 of the finger rest 32 on the other hand. This enables control of the surface S of the retention device 4.

In prior art syringes, in particular those in which the body is made of a rigid material, the piston retaining functions are usually supported by structures created directly in the body of the syringe. Since these structures nevertheless have to allow the passage of the piston into the body of the syringe and the extraction from the mold of the body during its production with an undercut, they do not sufficiently fulfill their retention function.

Moreover, the retention device 4 is mounted in the body without necessitating the passage of a hard spot, such as is produced by an annular boss in the syringe body, and as a result the sealing system 35 of the piston 3 is not damaged. In other words the assembly sequence of the syringe 1 does not degrade the sealing system 35 between the body 2 and the head 33 of the piston 3. The retention device 4 is assembled after the piston 3 is mounted in the body 2.

The body 2 of the syringe has a simple geometry. By a body 2 with a "simple geometry" is meant in the context of the present invention that this body 2 does not have any undercut. The mold for injection molding of the body 2 of the syringe 1 is therefore simpler and more reliable.

Moreover, the retention device 4 makes it possible to improve the guidance of the piston 3 into the retracted position, i.e. toward the rear relative to the piston head, which contributes to guaranteeing sealing even if the user moves the piston 3 off axis.

In the context of the invention the variants described can be combined with one another at least in part.

The invention claimed is:

1. A syringe comprising:

a body delimiting a chamber;

a piston able to slide in the chamber [of the body] along a longitudinal axis of the syringe, the piston comprising a rod, a head and a finger rest, which are all in one piece*, the head of the piston having a diameter that is sealingly received in a diameter of the chamber*; and a retention device that is deformable, wherein the retention device is force-fitted assembled in the chamber, wherein the retention device extends around the rod of the piston over an angular sector strictly greater than 180° when the retention device is assembled in the chamber, wherein the retention device is designed to come in contact with the head of the piston to prevent the piston from leaving the body entirely when the retention device is assembled in the chamber, wherein when the retention device is assembled in the chamber, the retention device has a passage into which the rod is received and into which the rod is axially movable for any angular position of the piston around the longitudinal axis, [and]

*wherein the retention device has no arrangement locking the retention device into a fixed closed ring form but comprises two C-shaped parts connected to each other by a thinned area which is deformable and which induces a spring effect between the C-shaped parts so as to make the retention device exert a radial force towards outside of the body when the retention device is assembled in the chamber,* wherein the retention device has protruding external ribs, which extend parallel to the longitudinal axis and which are plastically deformable when the retention device is assembled in the chamber*, and*

*wherein the retention device excluding the external ribs has a maximum transverse outside dimension that is less than the diameter of the chamber when the retention device is assembled in the chamber*.

2. The syringe of claim 1, wherein the body is made of a plastic material having a Young's modulus strictly greater than 1600 MPa.

3. The syringe of claim 1, wherein the retention device is force-fitted *assembled* axially in the chamber.

[4. The syringe of claim 1, wherein the retention device comprises two C-shaped parts connected to each other by a deformable thinned area.]

5. The syringe of claim 1, wherein the head has a diameter that is at least 10% greater than a diameter of the passage when the retention device is assembled in the chamber.

6. The syringe of claim 1, wherein the external ribs are arranged on the retaining device and distributed at a distance from one another around the longitudinal axis.

7. The syringe of claim 1, wherein at each of the external ribs, the retention device has a maximum outside transverse dimension that is strictly greater than a diameter of the chamber when the retention device is assembled in the chamber.

8. The syringe of claim 1, wherein *the body is provided with a housing leading into the chamber, and wherein* the retention device includes at least one external clip which is [engaged transversely in a housing of the body when the retention device is assembled in the chamber] *adapted:*

*when the retention device is assembled in the chamber, to be received in the housing, and*

*when force-fitting the retention device in the chamber, to be urged radially toward the longitudinal axis by the body, until reaching the housing into which the at least one external clip engage transversely to the longitudinal axis by stress releasing.*

9. The syringe of claim 1, wherein the passage includes a lateral entry opening having a width that is less than a diameter of the rod both before and when the retention device is assembled in the chamber.

10. The syringe of claim 1, wherein the head includes a sealing element.

11. The syringe of claim 10, wherein the head includes a groove in which the sealing element is disposed.

12. The syringe of claim 10, wherein the sealing element is an integral part of the head.

13. The syringe of claim 1, wherein the volume of the chamber is less than 25 mL.

14. A method for assembling the syringe of claim 1, the method comprising:

(a) deforming [the retention device] *the thinned area to move the two C-shaped parts away from each other and then to move the two C-shaped parts toward each other so as* to mount the retention device around the rod;

(b) inserting the piston with the retention device mounted around the rod in the chamber; and (c) force fitting the retention device in the chamber.

15. The method of claim 14, wherein step (c) further comprises assembling the retention device to the body by a translation movement[.] *that is* coaxial with the longitudinal axis.

16. The syringe of claim 1, wherein in a geometrical plane that is perpendicular to the longitudinal axis, a minimum dimension of the passage is strictly greater than a maximum dimension of the rod all along the rod.

17. The syringe of claim 1, wherein the retention device has a surface which is perpendicular to the longitudinal axis and which is designed to come in contact with the head to prevent the piston from leaving the body entirely when the retention device is assembled in the chamber.

18. A syringe comprising:

a body delimiting a chamber;

a piston able to slide in the chamber [of the body] along a longitudinal axis of the syringe, the piston comprising a rod, a head and a finger rest, which are all in one piece, *the head of the piston having a diameter that is sealingly received in a diameter of the chamber*; and a retention device that is deformable, wherein the retention device is force-fitted assembled in the chamber, wherein the retention device extends around the rod of the piston over an angular sector strictly greater than 180° when the retention device is assembled in the chamber, wherein the retention device has a surface which is perpendicular to the longitudinal axis, which has a closed ring shape and which is designed to come in contact with the head to prevent the piston from leaving the body entirely when the retention device is assembled in the chamber, [and]

*wherein the retention device comprises two C-shaped parts connected to each other by a thinned area that is deformable,* wherein the retention device has protruding external ribs, which extend parallel to the longitudinal axis and which are plastically deformable when the retention device is assembled in the chamber, *and*

*wherein the retention device excluding the external ribs has a maximum transverse outside dimension that is less than the diameter of the chamber when the retention device is assembled in the chamber.*

19. The syringe of claim 18, wherein when the retention device is assembled in the chamber, the retention device has a passage into which the rod is received and into which the rod is axially movable for any angular position of the piston around the longitudinal axis.

20. The syringe of claim 18, wherein the body is made of a plastic material having a Young's modulus strictly greater than 1600 MPa.

21. The syringe of claim 18, wherein the retention device is force-fitted *assembled* axially in the chamber.

[22. The syringe of claim 18, wherein the retention device comprises two C-shaped parts connected to each other by a deformable thinned area.]

23. The syringe of claim 18, wherein the external ribs are arranged on the retaining device and distributed at a distance from one another around the longitudinal axis.

24. The syringe of claim 18, wherein at each of the external ribs, the retention device has a maximum outside transverse dimension that is strictly greater than a diameter of the chamber when the retention device is assembled in the chamber.

25. The syringe of claim 18, wherein the volume of the chamber is less than 25 mL.

26. A method for assembling the syringe of claim 18, the method comprising:

(a) deforming [the retention device] *the thinned area to move the two C-shaped parts away from each other and then to move the two C-shaped parts toward each other so as* to mount the retention device around the rod;

(b) inserting the piston with the retention device mounted around the rod in the chamber; and (c) force fitting the retention device in the chamber.

27. The method of claim 26, wherein step (c) further comprises assembling the retention device to the body by a translation movement[.] *that is* coaxial with the longitudinal axis.

*28. The syringe of claim 18, wherein the body is provided with a housing leading into the chamber, and wherein the retention device includes at least one external clip which is adapted:*

*when the retention device is assembled in the chamber, to be received in the housing, and*

*when force-fitting the retention device in the chamber, to be urged radially toward the longitudinal axis by the body, until reaching the housing into which the at least one external clip engage transversely to the longitudinal axis by stress releasing.*

*29. The syringe of claim 18, wherein the retention device has no arrangement locking the retention device into a fixed closed ring form, and wherein the thinned area induces a spring effect between the C-shaped parts so as to make the retention device exert a radial force towards outside of the body when the retention device is assembled in the chamber.*

*30. A method for assembling a syringe,*

*the syringe comprising:*

*a body delimiting a chamber;*

*a piston able to slide in the chamber along a longitudinal axis of the syringe, the piston comprising a rod, a head and a finger rest, which are all in one piece the head of the piston having a diameter that is sealingly received in a diameter of the chamber; and*

*a retention device that is deformable,*

*wherein the retention device is force-fitted assembled in the chamber,*

*wherein the retention device extends around the rod of the piston over an angular sector strictly greater than 180° when the retention device is assembled in the chamber, wherein the retention device is designed to come in contact with the head of the piston to prevent the piston from leaving the body entirely when the retention device is assembled in the chamber,*

*wherein when the retention device is assembled in the chamber, the retention device has a passage into which the rod is received and into which the rod is axially movable for any angular position of the piston around the longitudinal axis,*

*wherein the retention device comprises two C-shaped parts connected to each other by a thinned area that is deformable,*

*wherein the retention device has protruding external ribs, which extend parallel to the longitudinal axis and which are plastically deformable when the retention device is assembled in the chamber, and*

*wherein the retention device excluding the external ribs has a maximum transverse outside dimension that is less than the diameter of the chamber when the retention device is assembled in the chamber,*

*and the method comprising:*

(*a*) *deforming the thinned area to move the two C-shaped parts away from each other and then to move the two C-shaped parts toward each other so as to mount the retention device around the rod;*

(*b*) *inserting the piston with the retention device mounted around the rod in the chamber; and*

(*c*) *force fitting the retention device in the chamber.*

* * * * *